United States Patent
Walker et al.

(10) Patent No.: US 9,057,600 B2
(45) Date of Patent: Jun. 16, 2015

(54) REDUCING INCREMENTAL MEASUREMENT SENSOR ERROR

(71) Applicant: Hansen Medical, Inc.

(72) Inventors: Sean P. Walker, Fremont, CA (US); Serena H. Wong, Mountain View, CA (US); June Park, Palo Alto, CA (US); Neal A. Tanner, Burnet, TX (US)

(73) Assignee: Hansen Medical, Inc., Mountain View, CA (US)

( * ) Notice: Subject to any disclaimer, the term of this patent is extended or adjusted under 35 U.S.C. 154(b) by 0 days.

(21) Appl. No.: 14/208,514

(22) Filed: Mar. 13, 2014

(65) Prior Publication Data

US 2014/0264081 A1 Sep. 18, 2014

Related U.S. Application Data

(60) Provisional application No. 61/779,742, filed on Mar. 13, 2013.

(51) Int. Cl.
*G01B 11/14* (2006.01)
*G01B 21/04* (2006.01)

(52) U.S. Cl.
CPC .............. *G01B 11/14* (2013.01); *G01B 21/045* (2013.01)

(58) Field of Classification Search
CPC .................. A61B 2019/5261; A61B 19/5244; A61B 5/065; G01B 11/14
USPC ....................................................... 250/459.1
See application file for complete search history.

(56) References Cited

U.S. PATENT DOCUMENTS

| | | |
|---|---|---|
| 5,398,691 A | 3/1995 | Martin et al. |
| 5,408,409 A | 4/1995 | Glassman et al. |
| 5,524,180 A | 6/1996 | Wang et al. |
| 5,553,611 A | 9/1996 | Budd et al. |
| 5,558,091 A | 9/1996 | Acker et al. |
| 5,631,973 A | 5/1997 | Green |
| 5,636,255 A | 6/1997 | Ellis |
| 5,713,946 A | 2/1998 | Ben-Haim |
| 5,729,129 A | 3/1998 | Acker |
| 5,749,362 A | 5/1998 | Funda et al. |
| 5,859,934 A | 1/1999 | Green |
| 5,873,822 A | 2/1999 | Ferre et al. |
| 5,876,325 A | 3/1999 | Mizuno et al. |
| 5,902,239 A | 5/1999 | Buurman |
| 5,920,319 A | 7/1999 | Vining et al. |

(Continued)

FOREIGN PATENT DOCUMENTS

WO         03086190 A1   10/2003
WO   WO 2011141829 A1 * 11/2011

*Primary Examiner* — Marcus Taningco
(74) *Attorney, Agent, or Firm* — Scott M. Smith; Dorsey & Whitney LLP

(57) ABSTRACT

For position sensors, e.g., a fiber-based system, that build a shape of an elongated member such as a catheter using a sequence of small orientation measurements, a small error in orientation at the proximal end of the sensor will cause large error in position at distal points on the fiber. Exemplary methods and systems are disclosed which may provide full or partial registration along the length of the sensor to reduce the influence of the measurement error. Additional examples are directed to applying selective filtering at a proximal end of the elongated member to provide a more stable base for distal measurements and thereby reducing the influence of measurement errors.

20 Claims, 6 Drawing Sheets

(56) References Cited

U.S. PATENT DOCUMENTS

| | | |
|---|---|---|
| 5,951,475 A | 9/1999 | Gueziec et al. |
| 6,016,439 A | 1/2000 | Acker |
| 6,019,724 A | 2/2000 | Gronningsaeter et al. |
| 6,226,543 B1 | 5/2001 | Gilboa et al. |
| 6,233,476 B1 | 5/2001 | Strommer et al. |
| 6,253,770 B1 | 7/2001 | Acker et al. |
| 6,259,806 B1 | 7/2001 | Green |
| 6,272,371 B1 | 8/2001 | Shlomo |
| 6,424,885 B1 | 7/2002 | Niemeyer et al. |
| 6,592,520 B1 | 7/2003 | Peszynski |
| 6,593,884 B1 | 7/2003 | Gilboa et al. |
| 6,711,429 B1 | 3/2004 | Gilboa et al. |
| 6,726,675 B1 | 4/2004 | Beyar |
| 6,782,287 B2 | 8/2004 | Grzeszczuk et al. |
| 6,892,090 B2 | 5/2005 | Verard et al. |
| 6,994,094 B2 | 2/2006 | Schwartz |
| 6,996,430 B1 | 2/2006 | Gilboa et al. |
| 7,155,315 B2 | 12/2006 | Niemeyer et al. |
| 8,460,236 B2 | 6/2013 | Roelle et al. |
| 8,821,376 B2 | 9/2014 | Tolkowsky |
| 2005/0033149 A1 | 2/2005 | Strommer et al. |
| 2005/0171508 A1 | 8/2005 | Gilboa |
| 2006/0025676 A1 | 2/2006 | Viswanathan et al. |
| 2006/0076023 A1 | 4/2006 | Rapacki et al. |
| 2006/0184016 A1 | 8/2006 | Glossop |
| 2007/0013336 A1 | 1/2007 | Nowlin et al. |
| 2007/0015997 A1 | 1/2007 | Higgins et al. |
| 2007/0055128 A1 | 3/2007 | Glossop |
| 2007/0135803 A1 | 6/2007 | Belson |
| 2007/0225559 A1 | 9/2007 | Clerc et al. |
| 2007/0265503 A1 | 11/2007 | Schlesinger et al. |
| 2007/0276180 A1 | 11/2007 | Greenburg et al. |
| 2007/0293721 A1 | 12/2007 | Gilboa |
| 2008/0212082 A1 | 9/2008 | Froggatt et al. |
| 2009/0137952 A1 | 5/2009 | Ramamurthy et al. |
| 2009/0262109 A1 | 10/2009 | Markowitz et al. |
| 2013/0030363 A1* | 1/2013 | Wong et al. .............. 604/95.04 |

* cited by examiner

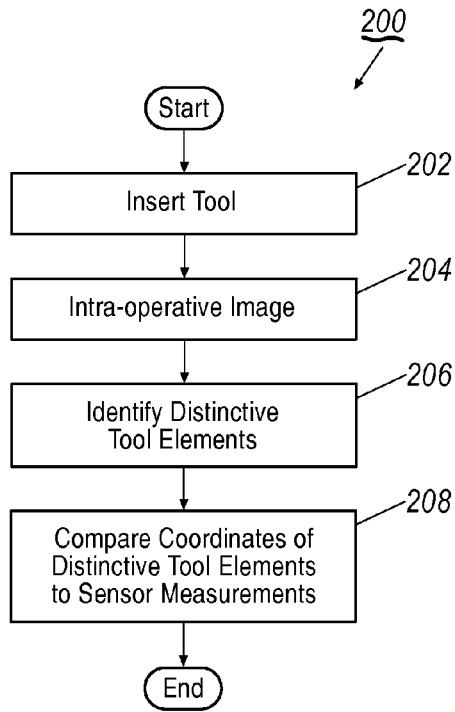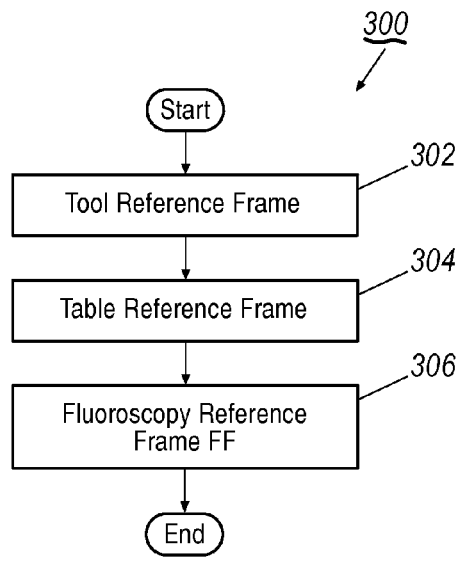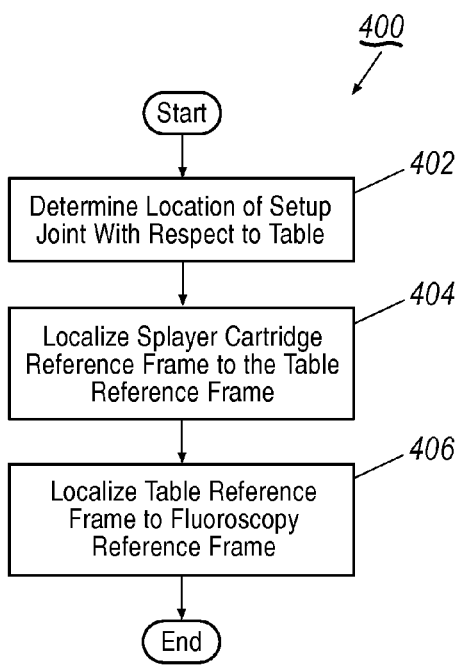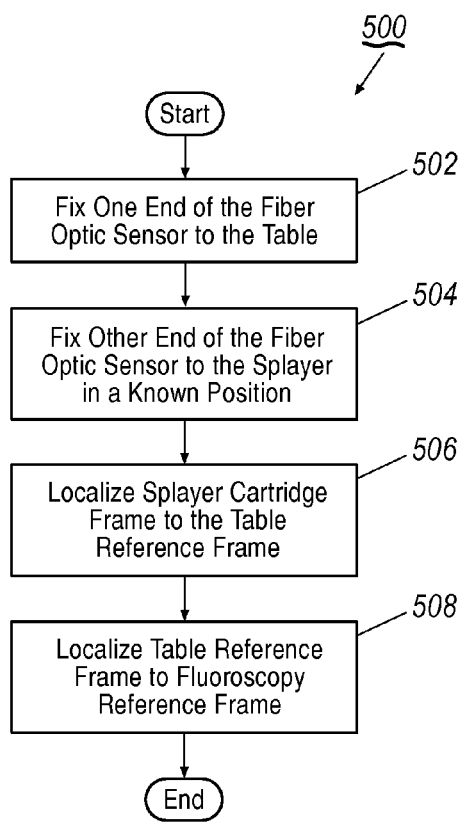
FIG. 4
FIG. 5
FIG. 6
FIG. 7

REDUCING INCREMENTAL MEASUREMENT SENSOR ERROR

CROSS-REFERENCE TO RELATED APPLICATIONS

This application claims priority to U.S. Provisional Patent Application No. 61/779,742, filed Mar. 13, 2013, the contents of which are hereby incorporated in their entirety.

BACKGROUND

Currently known minimally invasive procedures for diagnosis and treatment of medical conditions use shapeable instruments, such as steerable devices, flexible catheters or more rigid arms or shafts, to approach and address various tissue structures within the body. For various reasons, it is highly valuable to be able to determine the 3-dimensional spatial position of portions of such shapeable instruments relative to other structures, such as the operating table, other instruments, or pertinent anatomical tissue structures. Such information can be used for a variety of reasons, including, but not limited to: improve device control; to improve mapping of the region; to adapt control system parameters (whether kinematic and/or solid mechanic parameters); to estimate, plan and/or control reaction forces of the device upon the anatomy; and/or to even monitor the system characteristics for determination of mechanical problems. Alternatively, or in combination, shape information can be useful to simply visualize the tool with respect to the anatomy or other regions, whether real or virtual.

In many conventional systems, the catheter (or other shapeable instrument) is controlled in an open-loop manner, as described in U.S. patent Ser. No. 12/822,876, the contents of which are incorporated by reference in its entirety. However, at times the assumed motion of the catheter does not match the actual motion of the catheter. One such reason for this issue is the presence of unanticipated or unmodeled constraints imposed by the patient's anatomy. Another reason for this may be that the parameters of the tool do not meet the ideal/anticipated parameters because of manufacturing tolerances or changes in the mechanical properties of the tool from the environment and aging.

Thus to perform certain desired applications, such as, for example, instinctive driving, shape feedback, and driving in a fluoroscopy view or a model, there exists a need for tool sensors to be properly registered to the patient in real time. Moreover, there remains a need to apply the information gained by spatial information or shape and applying this information to produce improved device control or improved modeling when directing a robotic or similar device. There also remains a need to apply such controls to medical procedures and equipment.

Localization sensors such as fiber optic shape sensors may include Incremental Measurement Sensors (IMSs). An IMS measures a shape or path of an elongate member by combining a sequence of serial orientation and distance measurements. For instance, FOSSL generates a shape by measuring types of strain at discrete points in the fiber; this strain is then translated to the incremental change in roll and bend, which is incremented along all steps to obtain the position and orientation at a given location. As a result, each position and orientation at a point is dependent on the position and orientation of all proceeding points. In contrast, an electromagnetic coil sensor measures position at points along the elongate member independent of any other measurements.

One drawback of IMSs is that a measurement noise (error) at any location along the path may propagate to all measurements distal to that measurement. While these errors are implicit in the nature of the sensor, orientation errors at a proximal portion of the IMS may result in a large position error at the distal end of the elongate member. In applications that include accurate distal position measurements, this can cause the measured tip position to vary greatly between successive measurements due to noise at a single point in the proximal portion. One way of thinking about the issue is to consider the IMS length as a lever arm—small rotations at one end cause large changes in the position at the other end. The longer the lever arm, the more pronounced the conversion from proximal orientation error to distal position error. It should be noted that an orientation error at the proximal end will not tend to cause a large orientation error at the distal end because orientation errors themselves accumulate (sum) over the length of the sensor.

Thus, for Incremental Measurement Sensors that build a shape using a sequence of small orientation measurements, a small error in orientation at the proximal end of the sensor will cause a large error in position at distal points on the fiber. Accordingly, there is a need for an improved method of using IMSs that reduces measurement errors.

SUMMARY

Exemplary systems and methods are disclosed for reducing measurement error, e.g., relating to position measurements of an elongated member, e.g., along a distal portion of the elongated member. An exemplary method includes providing an incremental sensor measurement at a distal position on an elongated member, and applying registration data at one or more proximal locations along the elongated member. This exemplary method may further include determining a position of the incremental measurement sensor based at least upon the registration data from the one or more proximal locations.

In another exemplary method, either alternatively or in addition to the above-described registration data, a proximal signal of the elongated member may be selectively filtered, e.g., in comparison to a distal portion of the elongated member. In such examples, a distal position of the incremental measurement sensor may be determined based at least upon the filtered proximal signal, thereby reducing a fluctuation of the determined distal position of incremental measurement sensor.

An exemplary measurement system may include an incremental sensor measurement positioned at a distal position on an elongated member, and a processor. In some exemplary approaches, the processor may be configured to apply registration data at one or more proximal locations along the elongated member, and to determine a position of the incremental measurement sensor based at least upon the registration data from the one or more proximal locations. In other examples, either alternatively or in addition to relying upon registration data, the processor may be configured to selectively filter a proximal signal of the elongated member, and determine a position of the incremental measurement sensor based at least upon the filtered proximal signal.

BRIEF DESCRIPTION OF THE DRAWINGS

While the claims are not limited to a specific illustration, an appreciation of the various aspects is best gained through a discussion of various examples thereof. Referring now to the drawings, exemplary illustrations are shown in detail.

Although the drawings represent the illustrations, the drawings are not necessarily to scale and certain features may be exaggerated to better illustrate and explain an innovative aspect of an example. Further, the exemplary illustrations described herein are not intended to be exhaustive or otherwise limiting or restricted to the precise form and configuration shown in the drawings and disclosed in the following detailed description. Exemplary illustrations are described in detail by referring to the drawings as follows:

FIG. 4 is a flow chart that illustrates a method of transforming a reference frame for a sensor of a surgical tool into a target reference frame.

FIG. 5 is a flow chart that illustrates a method of transforming a reference frame associated with a tool into a target reference frame.

FIG. 6 is a flow chart that illustrates a method of transforming a reference frame associated with a tool into a target reference frame utilizing medical appliances.

FIG. 7 is a flow chart that illustrates a method of using a sensor to transform a reference frame associated with a tool into a target reference frame.

DETAILED DESCRIPTION

Figure 1A:
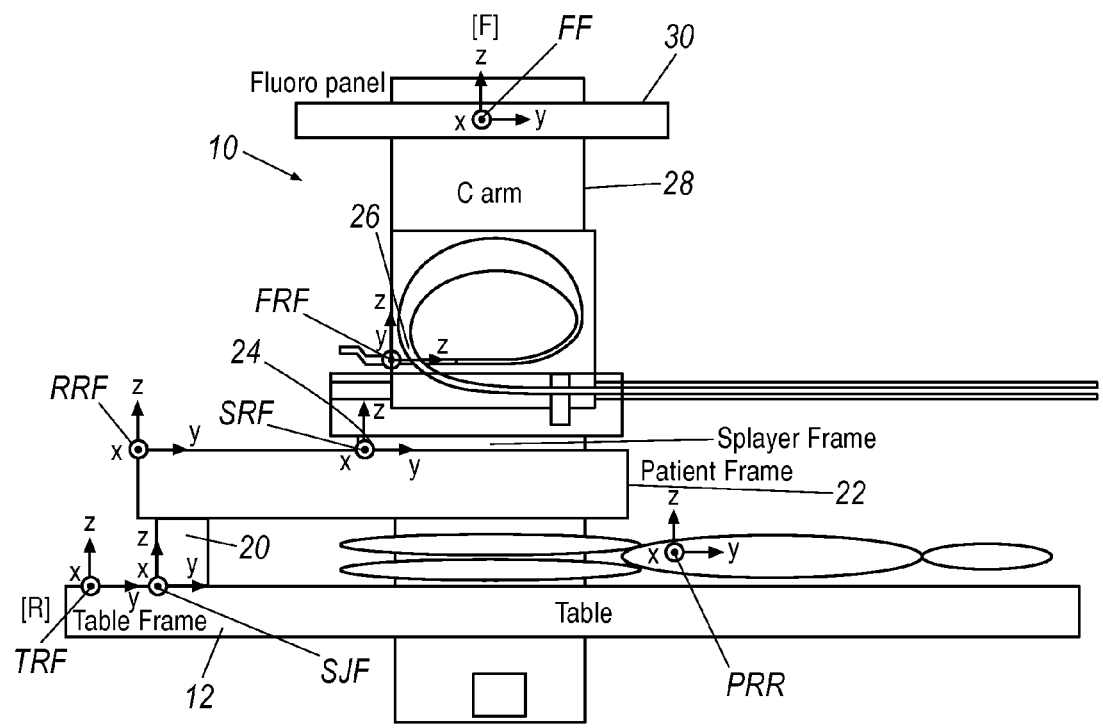
FIG. 1A illustrates a variation of a localization system in a typical operation room set up.

Exemplary approaches described herein provide full or partial registration along the length of a sensor to reduce the influence of measurement error. As will be described further below, an exemplary registration process generally relates a reference frame of a sensor to another reference frame of interest. Alternatively or in addition to examples employing full or partial registration along the length of a sensor, applying heavier filtering at the proximal end of the sensor can provide a more stable base for distal measurements reducing the influence of measurement errors. While these exemplary approaches are discussed in the context of a Fiber Optic Shape Sensing and Localization (FOSSL) system, other visualization methodologies may be employed. Fiber optic shape sensing is a technology that can sense the shape of a flexible body such as a catheter during a surgical procedure to permit visualization of the catheter in the patient's anatomy.

One exemplary methodology provides a solution to this problem by using point registration along the length of the fiber to reduce the effect of the lever arm problem. As noted above, these techniques apply to all sensors that use incremental measurements, but nevertheless exemplary approaches below are described generally in the context of FOSSL fiber technology.

Another exemplary approach includes applying registration data along the fiber as well as at the proximal attachment to reduce error. Additionally, in another example stronger filtering may be utilized on the proximal orientation signal to reduce noticeable fluctuation of the position distally.

In still another exemplary illustration, orientation error at the proximal end of an IMS is decoupled from position error at the distal end. Exemplary methods of decoupling this error include providing some notion of a registration closer to the distal tip and reduce the effect of orientation error.

Various localization systems and methods for tracking an elongate instrument or tool, e.g., a robotically controlled elongate instrument, in real time, in a clinical or other environment, are described herein. The term "localization" is used in the art in reference to systems for determining and/or monitoring the position of objects, such as medical instruments or tools in a reference coordinate system. Various instruments are contemplated for use in the various systems described herein. In one exemplary arrangement, elongate instruments are contemplated, such as, e.g., a catheter or vascular catheter. The various methods and systems may include integrating or registering a localization system or a localization sensor coupled to a surgical tool, with an image. A fiber optic tracking or localization system is just one, non-limiting example of a system that allows for the tracking of a location, position and/or orientation of a localization sensor placed. Various other localization sensors may be utilized, e.g., electromagnetic sensors, and other sensors for detecting or controlling the movement of medical equipment. When the localization sensor is integrated into an image, it enhances the capabilities of an instrument control or tracking system by allowing a user or doctor to easily navigate the instrument through the complex anatomy without exposing the patient to excessive radiation over a prolonged period of time.

The localization data or tracking information of a localization sensor may be registered to the desired image or model to allow for navigation of an elongate instrument through the image or model to accurately represent movement of the elongate instrument within a patient. As noted above, registration is a process that generally requires relating a reference frame of a sensor to another reference frame of interest. If the positions, orientations or shapes of two or more objects are known in the same reference frame, then the actual positions, orientations or shapes of each object relative to each other may be ascertained. Thus, with this information, one can drive or manipulate one of the objects relative to the other objects.

In most interventional procedures, the reference frame of interest is the visualization frame. The reference frame is the frame that the doctor is viewing, such as a patient or a live 2D/3D image such fluoroscopy, ultrasound or others. Thus, the goal of registration is to determine the relationship of a frame of a sensor integrated into a tool or element in the surgical suite within the frame of reference of the patient, as represented in a 2D/3D image.

When the tool is registered to a 3D model, the user can drive and manipulate the tool in the 3D model. This technique provides an advantage in that there is no longer a need for live fluoroscopy and radiation during a procedure. The tool is localized to the 3D model and the position, shape and orientation of the tool is visible to the user. Since the tool position, shape and orientation is updated in real time by a localization sensor, an image of the tool in the virtual representation of the 3D model will be updated as it is being advanced into the patient. The sensor is localized to the reference frame of the 3D model; therefore the orientation of a tip of the tool is known relative to the 3D model. This enables driving of the tool (such as a catheter) within 3 dimensional views of the anatomy and hence improves visualization and control during a surgical procedure.

As discussed above, exemplary sensors may include incremental measurement sensors, where the position and orientation of a particular point is calculated and dependent on the previously calculated orientations and positions of proximal points or (spacing of consecutive points). Thus, the localization sensor operating in any medical system needs to be registered with a coordinate system, frame or image that is useful to an operator, such as the pre-operative 3D model or a fluoroscopic image. For incremental measurement sensors, such registration is challenging because the coordinate system or frame of the sensor is not always easily related to the coordinate system of interest (i.e., the pre-operative 3D model).

Moreover, the relationship between the sensor and the coordinate system of the interest may change over time during a procedure. For example, in one exemplary robotic system, a fiber optic sensor may have its reference frame based physically in a splayer (base) for a catheter. Thus, as the splayer is robotically driven during a surgical procedure, the position and orientation of the base of the fiber will change with respect to other reference frames.

In addition to changing positions of reference frames, the registration process often requires information about the imaging system providing the image, such as its physical dimensions and/or the details about the imaging techniques used to acquire a particular 3D model or other image. Due to the variability in equipment used in a clinical environment, in certain situations there may be no guarantee that such information will be available or easily obtainable to an outside party.

As such, various techniques to estimate system parameters and various registration techniques may help facilitate the clinical use of localization technology.

In certain variations, a method for tracking a robotically controlled elongate instrument in real time may include displaying an image of a patient's anatomy. A localization sensor may then be coupled to the robotically controlled instrument. The localization sensor may provide localization data of the sensor and/or instrument. Moreover, different sensors may be registered to specific tools, thereby enabling tool differentiation. The localization data from the localization sensor may be registered to the image. Registering may include transforming localization data generated by the localization sensor to the coordinate system or frame of the image such that localization data of the elongate instrument, to which the localization sensor is coupled, is overlaid on the image. The coordinate system of the localization sensor may be transformed or translated to the coordinate system of the image through one or more transformations, and optionally through other coordinate systems, to register the localization data to the image. As a result, a continuously or substantially continuously updated location of at least a portion of the elongate instrument is provided in the image of the anatomy of a patient, which allows for or facilitates robotic navigation or control of the elongate instrument through the anatomy e.g., through the vasculature of a patient.

The location, position and/or orientation of the localization sensor may be continuously tracked to allow for accurate manipulation of the elongate instrument in or through the anatomy of a patient. Various types of images may be utilized in the methods and systems described herein. For example, an image may be generated by CT or 2D or 3D fluoroscopy. An image may include a 3D or 2D anatomical model or a 2D or 3D fluoroscopic image or other types of images useful for visualizing an anatomy of a patient to perform various medical procedures.

When using a fluoroscopy image, an image intensifier may be utilized. Localization data from the localization sensor may be registered to a fluoroscopy coordinate system of a fluoroscopy image coupled to the image intensifier. In order to register the localization data from the localization sensor to the fluoroscopy image, various parameters may be ascertained or known. For example, such parameters may include: a distance from an X-ray source to the image intensifier, a distance from the source to a bed, a size of the image intensifier, and/or the axis of rotation of a C-arm of the fluoroscopy system.

In certain variations, localization data can be registered to a 3D anatomical model or a fluoroscopy image. The techniques used to perform the registration vary depending on the target. Where localization data is registered to a fluoroscopy image, the 2D nature of the fluoroscopy images may require that multiple images be taken at different angles before the registration process is complete.

FIG. 1A is a schematic of a typical operation room set up for a robotic surgical system. More specifically, a typical robotic surgical system 10 includes a table 12 upon which a patient 14 will be placed, a fluoroscopy system 16, and a surgical tool, such as a catheter 18 (best seen in FIG. 2). Attached to the table 12 is a setup joint arm 20 to which a remote catheter manipulator (RCM) 22 is operatively connected. A splayer 24 may be mounted to the RCM 22. A surgical tool, such as a catheter, is operatively connected to the splayer 24. A fiber sensor 26 may be operatively connected to the surgical tool. The fluoroscopy system 16 includes a C-arm 28. A fluoroscopy panel 30 is mounted to the C-arm 28. The C-arm is selectively moveable during the procedure to permit various images of the patient to be taken by the fluoroscopy panel 30.

Figure 2:
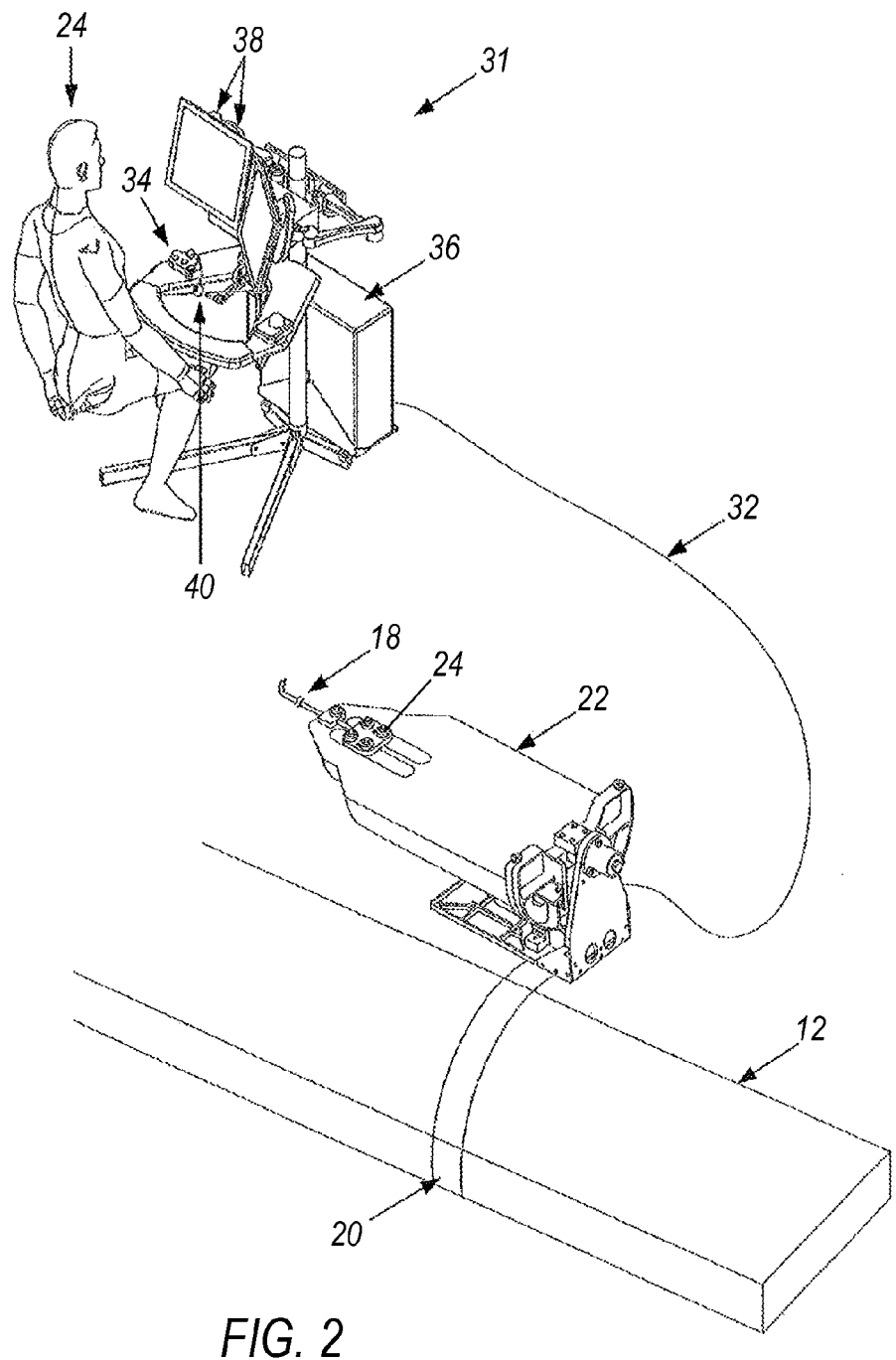
FIG. 2 illustrates an exemplary robotic surgical system.

Additional portions of the robotic surgical system 10 may be further seen in FIG. 2. More specifically, robotic surgical system 10 may further comprise an operator control station 31, which may be remotely positioned with respect to table 12. A communication link 32 transfers signals between the operator control station 31 and the RCM 22. The operator control station 31 includes a control console 34, a computer 36, a computer interface, such as a mouse, a visual display system 38 and a master input device 40. The master input device 40 may include, but is not limited to, a multi-degree of freedom device having multiple joints and associated encoders.

Figure 1B:
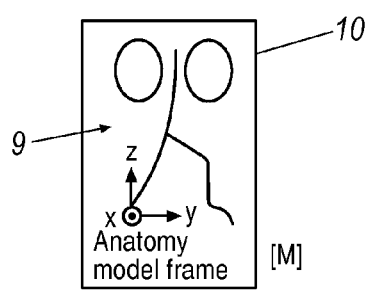
FIG. 1B illustrates a 3D Model frame.

Each element of the robotic surgical system 10 positioned within the operating suite may define a separate reference frame to which sensors may be localized. More specifically, separate reference frames may be defined for each of elements of the robotic surgical system 10. Such reference frames may include the following: a table reference frame TRF for the table 12, a setup joint frame SJF for the setup joint 20, an RCM reference frame RRF for the remote catheter manipulator (RCM) 22, a splayer reference frame SRF, a fluoroscopy reference frame FF. Separate reference frames may also be defined for a patient—patient reference frame PRR, a reference frame FRF for a sensor disposed within a surgical tool, and a pre-operative 3D frame AMF (best seen in FIG. 1B).

To relate a coordinate frame of a fiber optic sensor of a tool to either a fluoroscopy frame FF, or a pre-operative 3D frame AMF, a variety of registration techniques may be employed. Generally, the techniques proposed herein fall into several categories. A first category involves using image processing or vision techniques to relate a reference frame RFR of a fiber sensor directly to an image or 3D model. This technique may be accomplished manually by a user or done automatically using image processing techniques. Another category to coordinate the reference frame FRF of a fiber optic sensor involves using knowledge about hardware, and potentially other sensors and or position of the fiber. Further discussion of these techniques is set forth below.

Registration to Fluoroscopy Coordinate Frame

Referring to the systems illustrated in FIGS. 1-3, the first category of registration techniques will now be described. The first category relates the coordinate system of the sensor reference frame FRF to a fluoroscopy reference frame FF directly. This technique utilizes fluoroscopy images taken during the surgical procedure by the fluoroscopy system 30, in real-time.

More specifically, an exemplary registration process 200 is illustrated in the flow chart of FIG. 4. The process 200 may begin by inserting a tool into a patient at block 202. As described above, in one exemplary configuration, the tool is a catheter 18, which may be inserted by an RCM 22. Next, at block 204 an intra-operative image is taken of the tool 18.

In one exemplary arrangement, the intra-operative image is a fluoroscopy image taken by fluoroscopy system 30. Next, distinctive elements of the tool may be identified in the fluoroscopy image at block 206. In one exemplary configuration, the block 206 may be accomplished by instructing the user to select certain marked points of a catheter 18 in the fluoroscopy image at the work station 31. Examples of marked points include, but are not limited to, physical features of the catheter 18 such as the tip of the catheter 18, certain shapes and an articulation band. In other exemplary configurations, fluoroscopy markers may be disposed on the catheter.

Once the selected points are identified in the fluoroscopy image, in the next step 208, coordinates of the selected points of the catheter 18 may be compared to corresponding measured points of elements of the catheter. In one exemplary configuration, measured points from a tool sensor operatively connected to the tool 18 may be used. More specifically, in one exemplary configuration, the tool sensor is a fiber optic sensor. Information about the fiber optic sensor will be known in relation to the features on the catheter from an in-factory calibration. This comparison can be used to determine a transformation matrix that can be used to transform a reference frame FRF for a sensor disposed within the surgical tool into the fluoroscopy reference frame FF. This transformation then localizes the tool relative to the intra-operative fluoroscopy image.

Once the fiber sensor of the tool has been registered or localized to the fluoroscopy image, the tool operator can now move or drive the tool to various, desired points visualized in the fluoroscopy image. Moreover, the computer 36 may be configured to track the marked points over time, such that an appropriate transformation may be updated.

In one exemplary configuration, the identifiable markers need not be on the portion of the tool that is inserted into the patient. For example, markers may be embedded on a splayer 24, which may allow for larger and more complex markers to provide enhanced registration capabilities.

As described above, in addition to utilizing fluoroscopy marked points, it is also contemplated that distinct shapes that may be visible under floursocopy may also be used. However, this technique will require some image segmentation (to identify and separate out targeted shapes).

With respect to the proposed technique of localizing a sensor reference frame FRF to the fluoroscopy reference frame FF, the localization sensor could serve to reduce the use of fluoroscopy during a procedure. More specifically, the use of fluoroscopy would be reduced since fluoroscopy would only be required when re-registration is needed during the procedure due to the loss of accuracy in the data obtained from the sensor.

Figure 3:
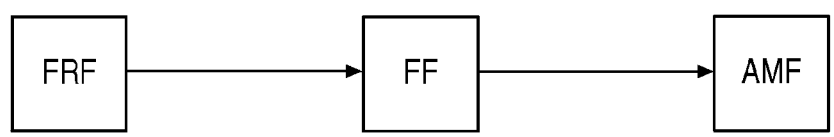
FIG. 3 is a schematic representation of a first registration technique of correlating a sensor reference frame to selective reference frames.

In certain arrangements, it may be desirable to further register the tool to a 3D model reference frame AMF, as illustrated in FIG. 3. Registration to the 3D Model is discussed more fully below.

Registration Through Successive Physical Components

Another exemplary technique proposed to register a tool 18 to a desired reference frame involves the use of physical components of the medical system 10 and multiplying successive transformations. This proposed technique 300 is illustrated schematically in FIG. 5 and involves finding a transformation path from a tool reference frame such as a fiber sensor, splayer 24, or catheter 18, to the table 12, as in most surgical suite setups, the table location is generally known with respect to the fluoroscopy system 30. More specifically, registration technique 300 involves determining a tool reference frame at block 302 (where the tool reference frame may be defined as the sensor reference frame FRF, splayer reference frame SRF or a catheter reference frame) and correlating the tool reference frame to a table reference frame TRF at block 304, thereby registering the tool 18 to the table 12. Registering the tool 18 to the table 12 will serve to provide necessary information to permit registration to an additional target frame, such as a fluoroscopy reference frame FF, for example. Because the table 12 location is typically known with respect to a fluoroscopy system 30, a comparison of set reference points of the table 12 with corresponding reference points in a fluoroscopy image may be used to determine a transformation matrix to transform the table reference frame TRF into the fluoroscopy reference frame FF. The tool 18 is registered to the table reference frame TRF, and thus combining all three transformations localizes the tool relative to the intra-operative fluoroscopy image.

However, it is understood that the present disclosure does not require that the tool 18 be registered to the table 12. Indeed, it is expressly contemplated that registration of the tool 18 to other physical components within the surgical suite may also be utilized. This proposed technique requires the use of other sensors in addition to, or alternative to a fiber sensor, however. Exemplary configurations of registration through physical surgical suite components are discussed in further detail below.

One exemplary method of performing registration through successive physical components is illustrated in the flow chart in FIG. 6. In this technique, the registration process 400 begins at block 402, with determining the location of the setup joint 20 with respect to the table 12. Encoders on the RCM 22 and setup joint 20, with kinematic models may be used to determine the location of the setup joint 20 with respect to the table 12. More specifically, the encoders assist with determining the location of the RCM 22 with respect to the table 12. With the location value of the position that the setup joint 20 is fixed to the table 12, the location of the splayer carriage 24 carried by the RCM 22 with respect to the table 12 can be determined; i.e., the setup joint reference frame SJF is localized with the RCM reference frame RRF. Because information about the catheter will be known in relation to the splayer carriage 24 from an in-factory calibration, at block 404 of the registration process 400, an evaluation of the splayer carriage 24 information with respect to the RCM can be used to determine a transformation matrix that can be used to transform the splayer carriage reference frame SRF to the table reference frame TRF. As described above, because the table 12 location is known with respect to the fluoroscopy system 30, at block 406 another transformation may be done from the table reference frame TRF to the fluoroscopy reference frame FF. This final transformation, i.e., from the table reference frame TRF to the fluoroscopy reference frame FF, then localizes the tool relative to the intra-operative fluoroscopy image.

In another exemplary method of performing registration through successive physical components, inertial sensors on the RCM 22, coupled with the information about the initial position of the RCM 22 on the table 12, may be used to assist in localizing the catheter splayer reference frame SRF to the table reference frame TRF. More specifically, once the RCM 22 is localized to the table reference frame TRF, the catheter splayer reference frame SRF may be localized to the table reference frame TRF, as the position of the catheter splayer 24 with respect to the RCM 22 will be known from in-factory calibration.

Yet another exemplary method 500 of performing registration through physical components is illustrated in FIG. 7. The method 500 uses a second fiber optic sensor. In a first step 502, one end of the fiber optic sensor is fixed to the table 12. Next, in step 504, the other end of the sensor is fixed to the splayer 24 in a known orientation/position. In this technique, a position and orientation transformation between the tip and base of the fiber sensor may be determined, thereby localizing the catheter splayer reference frame SRF to the table reference frame TRF in step 506. However, it is understood that the initial position of the fixed point at the table must be known. Once the catheter splayer reference frame SRF is localized to the table reference frame TRF, because the table 12 location is known with respect to the fluoroscopy system 30, in step 508 another transformation may be done from the table reference frame TRF to the fluoroscopy reference frame FF. This final transformation, i.e., from the table reference frame TRF to the fluoroscopy reference frame FF, then localizes the tool relative to the intra-operative fluoroscopy image.

A further exemplary method of performing registration of a surgical tool to a physical component includes using electromagnetic sensors to track the location of the splayer 24 with respect to an electromagnetic sensor at a known location on the table 12. In using this technique, because the tool location is calibrated to the splayer 24 in the factory, once the splayer 24 is localized to the table reference frame TRF, the tool may be localized to the fluoroscopy reference frame FF as the table 12 is known with respect to the fluoroscopy system 30.

In yet another exemplary method, instead of electromagnetic sensors, overhead cameras or other visualization techniques may be employed to track distinct features on the splayer 24 and the table 12 to determine the respective orientation and position with regard to each other.

A further technique may use the range sensors (such as, e.g., IR or ultrasound) to find the distance to several distinct and predetermined points on the table 12 and the splayer 24. Once the splayer 24 is localized to the table reference frame TRF, the tool may be localized to the fluoroscopy reference frame FF as the table 12 is known with respect to the fluoroscopy system 30.

All of the above techniques serve to register the tool to a physical component within the surgical suite, such as, for example, the table 12. Some of the above techniques require the RCM 22 and setup joint 20 to be registered to the table 12. That pre-registration step may be achieved by using some known feature on the table 12 that the setup joint 20 may reference. Additionally, the pre-registration step may be achieved if the setup joint is equipped with joint sensors such as encoders. In another exemplary configuration, the tip of a sensor equipped tool may be used to touch or register the known feature on the table 12 to locate the table 12 with respect to other equipment within the surgical suite.

The kinematics of the RCM 22 can also be calculated by holding the tip of a fiber optic equipped tool in an arbitrary fixed location and cycling through the various axes of the RCM 22. By keeping the tip in a fixed location, the relative changes to the fiber origin can be observed, and thus the kinematics of the system can be determined and localized to the table 12. Once localized to the table reference frame TRF, the tool may then be localized to the fluoroscopy reference frame FF, as discussed above.

In addition to adding the sensors discussed in the above techniques, additional modifications may be made to the location of the fiber base to facilitate registering the fiber sensor to the physical structure within the suite, such as, for example, the table 12. For example, one modification is to extend the length of a fiber in the catheter so that the origin/base can be extended out of the splayer 24 and attached to a fixture having a known location on the table 12. Once localized to the table reference frame TRF, the tool may then be localized to the fluoroscopy reference frame FF, as discussed above.

Registration to a 3D Model

Registration of the tool to a 3D Model is also contemplated in this disclosure. Such registration may be performed directly from the fiber sensor reference frame FRF to the 3D Model frame AMF. In one exemplary technique, the operator is utilized. When the tool (such as the catheter) is inserted into the patient, tortuosity can be visualized from the fiber sensor data, as well as on the pre-operative 3D Model. To register the tool in the 3D Model, the operator may translate and rotate the 3D Model so that distinct images and/or features in the tortuosity match or line up with the shape of the fibers. However, in using this technique, every time the patient moves, the tool should be re-registered.

In another exemplary arrangement, rather than having an operator manually match features in the tortuosity, in one technique, a computer algorithm such as automated geometric search or mathematical optimization techniques that segments the model and matches the model and tool shape dynamically may also be used to match various shapes or features from the fiber sensor to the 3D pre-operative Model. However, if the patient moves, even slightly, the 3D Model could be mis-registered. Thus, the algorithms may be used to re-register the tool automatically or the user could use an input device, such as a track ball or mouse to move the 3D Model manually.

Another proposed technique may be used to register the fiber sensor to the 3D Model through the fluoroscopy image, as illustrated in FIG. 3. In this technique, any of the above described techniques for registering the surgical tool 12 to the fluoroscopy reference frame FF may be utilized. To register the fluoroscopy reference frame FF to the 3D Model reference frame AMF, in one exemplary configuration, specific anatomical landmarks may be used to provide recognizable reference points. The only requirement for this approach is to have an anatomical landmark that is recognizable in both the fluoroscopy reference frame FF, as well as the pre-operative 3D Model reference frame AMF. Once the recognizable point is identified in the fluoroscopy image, the 3D Model may then be rotated by the operator to line up the recognized points in the fluoroscopy images with the 3D Model images. This action serves to register the fluoroscopy reference frame FF to the frame of the 3D Model AMF. As the tool has previously been localized to the fluoroscopy reference plane FF, so once the fluoroscopy reference plane FF is registered, the tool's location within the patient's anatomy may be determined with reference to the 3D Model localizing the tool to the 3D Model. In one exemplary configuration, a visual representation of the tool, based on the transformation matrix, may be displayed on the 3D Model. In this manner, the tool operator may then navigate the tool through the 3D Model.

While certain of the above described techniques utilized distinct marked points of a tool, such as a medical catheter, to register the tool with the fluoroscopy image, it is also understood that registration of the tool may occur based on the location of the tool at the distinct anatomical landmarks. In other words, as the tip of the tool can be driven to a known anatomical location in the patient, the 3D Model may then be rotated by the user to overlay the known anatomical location in the 3D Model with the fluoroscopy image, in which the known anatomical location is visible. Such action will also serve to register the tool with the 3D Model or localize the tool in the reference frame of the 3D model reference frame AMF.

In another exemplary configuration, instead of, or in addition to, having the user manually rotate the 3D Model to correspond with the fluoroscopy image to line up distinct landmarks visible in both the fluoroscopy image and the 3D Model, the computer 36 may be programmed to employ a suitable algorithm such as automated geometric search or mathematical optimization techniques configured to match a distinct shape measured by the fiber sensor with a corresponding shape in the 3D Model. In this manner, the tool may also be registered with the 3D Model. The accuracy of this method will depend on the size of vessel that the tool is in, and the degree of curvature of the tool. Accuracy will be improved if the tool is in a smaller vessel and will be worse if the tool is in larger vessels. This automated technique can also be used in conjunction with the manual techniques described above. For example, the computer may be programmed to do automatic registration and suggest a preferred registration but the user may do final adjustments of the model. Once the tool is localized in the 3D Model of the patient's anatomy, the user may then proceed to maneuver the tool in the 3D Model.

Another technique that may be utilized to register the tool to the 3D Model through fluoroscopy system 30 involves the use of radiopaque markers. More specifically, radiopaque markers can be fixed to the anatomy. However, these markers would need to be present during pre-operative imaging when the 3D Model is created, and remain in the same location during intraoperative fluoroscopy imaging. With this technique, the position of these markers in the fluoroscopy reference frame FF can be used to correlate to the same markers in the 3D Model reference frame AMF, thereby registering the fiber sensor to the 3D Model reference frame AMF. Three-dimensional angiography may also make it easier to register the tool to the 3D Model by facilitating acquisition of the model in realtime, i.e. while the patient is on bed. While the model might drift away from the real anatomy when the operation is carried out, it may be advantageous to obtain the model and perform operations in the same spot.

Another technique that may be utilized to register the surgical tool to a 3D Model utilizes intravascular imaging. This technique allows for 3D visualization of a surgical tool, such as, a catheter, in the anatomy, but without the use of fluoroscopic imaging. Such a technique can benefit both physicians and patients by improving the ease of tool navigation, as well as and reducing radiation exposure of personnel inside the operating room.

Figure 8:
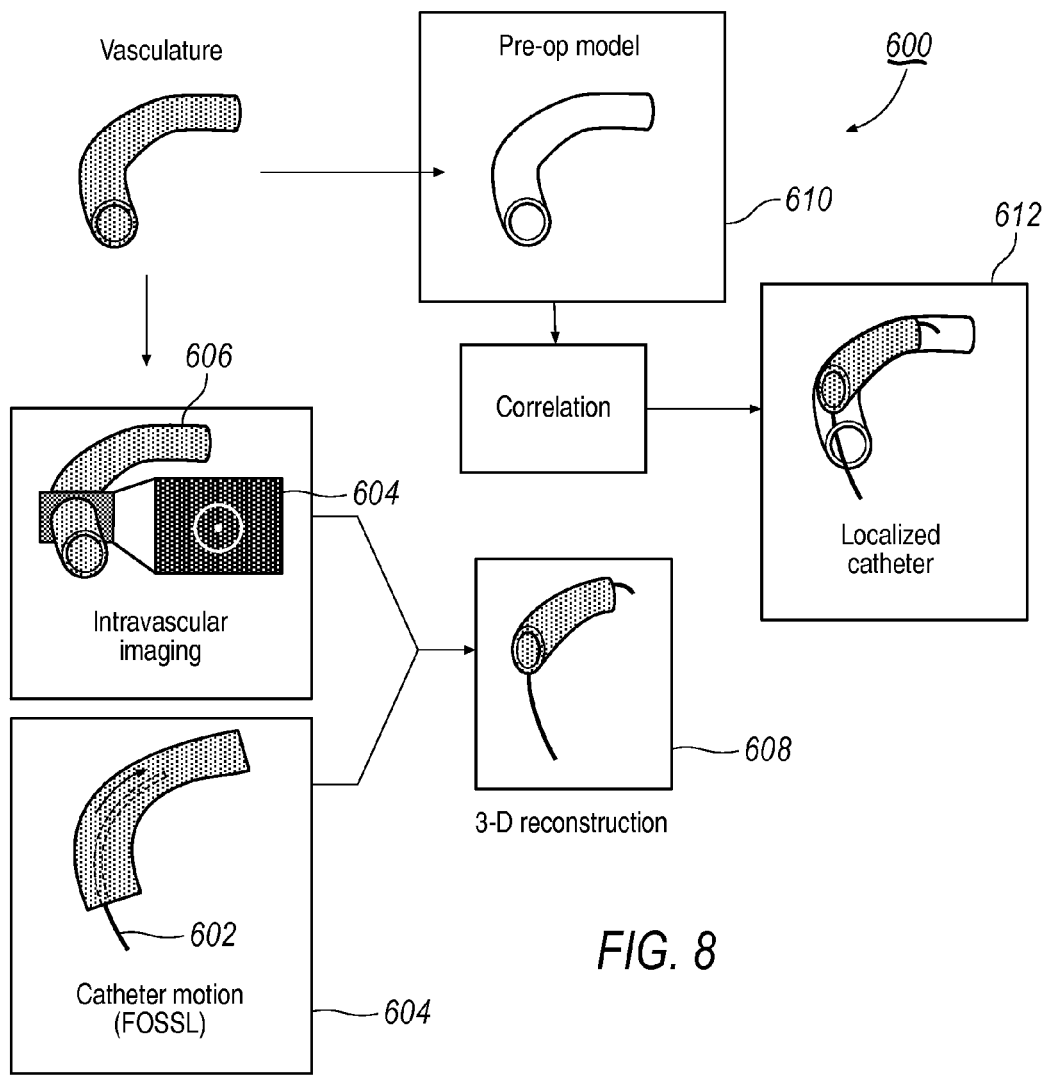
FIG. 8 is a schematic illustration of a method of using an intravascular imaging sensor coupled with a shape sensor to transform a reference frame associated with a tool into a target reference frame.

Turning now to FIG. 8, the registration technique 600 may begin by utilizing a sensor 602 operatively coupled to the tool to sense a shape of the tool 604 while in the patient. This sensed shape is then mathematically correlated against features of the vascular model such as centerlines or walls in which a larger correlation value corresponds to a better match. The correlation can be performed in real-time on each shape or by batch processing a sequence of shapes. This proposed technique assumes that the tool will always follow a unique configuration through the vasculature, and thus, a global maximum for the correlation exists. However, the correlation may return many local maxima since the tool configuration may follow many different paths between fixed distal and proximal ends. Choosing an incorrect maximum introduces registration error. Furthermore, in some cases, the pre-operative 3D model may differ from the actual vasculature for a number of reasons, including, for example, patient motion or inaccuracies in pre-operative sensing. Such situations also may lead to registration error.

Recent advances in intravascular imaging technology have brought about sensors 604 that can provide information about the local structure of vessel walls 606. Such information may be used for shape registration and environmental mapping. Two examples of these sensors are intravascular ultrasound (IVUS) probes, and optical coherence tomography (OCT). Intravascular ultrasound periodically produces a 2-D cross-sectional view of the blood vessel either to the sides of the catheter in standard IVUS or to the front of a catheter in Forward-Facing IVUS. Optical Coherence Tomography periodically produces a local 3D view of the vessel into which the tool is inserted. The images produced by these technologies may be processed to provide an estimate of a curve or surface representing the vessel wall 606. The sensors 604 may also determine the location of the catheter's endpoint within the vascular cross-section. Use of the sensors coupled with the tool 602 to provide shape information coupled with information obtainable from sensors 604 configured to provide information about the vessel walls 606 can assist in defining the 3D shape of the blood vessel 608.

Once the shape of the vessel is defined or otherwise reconstructed using the combined sensor data, the shape can be mathematically correlated to the 3D model 610, thereby registering the tool to the 3D Model 612. In implementation, the 3D reconstruction and correlation steps may be combined into a single recursive filtering algorithm. A Bayesian filter (e.g. Extended Kalman Filter (EKF), Unscented Kalman Filter (UKF), or Particle Filter) may be used to develop an estimate of the tool's position relative to the pre-op 3D model given both imaging and sensor 602 information. The filter's state is a set of points or a parametric curve representing the position and shape of the tool 602 with respect to the pre-op 3D model, as well as the rate of change of this shape. For accurate registration, patient motion may also be taken into account. Thus, the filter's state may also contain warping parameters for the pre-op 3D model. These warping parameters may be evenly distributed, or may be selected based on the structure of the anatomy around the vasculature. The motion of the structure of the anatomy around the vasculature may be measured using visible light tracking technologies such as stereoscopic cameras, structured light tracking technologies, and/or other localization technologies attached to the patient skin.

The recursive filtering algorithm operates by predicting the motion of the tool in the 3D model, then performing an update of the filter hypothesis given new sensor measurements. At each time-step, a kinematic model of the catheter and control inputs such as current pull-wire tension and displacement may be used to perform the filter's motion update. The filter's measurement update may apply a correction to the tool registration and model warping parameters by comparing a predicted vessel wall with the sensed position and orientation of the vessel from the imaging and sensor measurements. The update effectively executes the correlation between 3-D sensor information and the 3D model. Performing these correlations repeatedly in a recursive filtering framework may provide a real-time catheter position estimate. Furthermore, the filter's parameters may be tuned such that differences between the measurements and the model over a small time constant (ms) will lead to changes in the catheter position estimate in order to filter out high-frequency sensor noise. Differences over a large time constant (seconds) may lead to changes in the model's warping parameters.

Thus, once the tool has been registered to the 3D model, the location of the tool within the 3D model may be determined, allowing an operator to drive the tool within the vasculature using the 3D model without requiring intra-operative fluoroscopy.

Sensors 604 may also be utilized to sense the environment around the tool. Thus, once the tool is registered to the 3D model, this environmental information, such as, for example, vascular occlusions may be displayed at the correct position in the 3D Model.

More specifically, after tool registration, the intravascular imaging sensor 604 provides a mechanism to sense and display features of the environment surrounding the tool without the use of fluoroscopy. There are many ways to display this information. One non-limiting option is to simply provide a display of a real-time view of the imaging sensor's output alongside a view of the catheter's location in the 3D model or superimposed on top of the 3D model. Another option may be to analyze the intravascular image to detect environmental changes. For example, IVUS image processing techniques can be used to detect areas of plaque in the image. This information can be used to annotate the IVUS image in order to alert the physician to environmental conditions. Since a combination of IVUS and sensor data 602 may provide 3D information on the structure of these plaque formations, the 3D pre-op model can also be annotated. In this way, the existing work that has used IVUS to perform vascular sensing may be leveraged by the combined IVUS and sensor system to provide a 3D view of the environment to the physician.

Exemplary Error Reduction Methods

Figure 9:
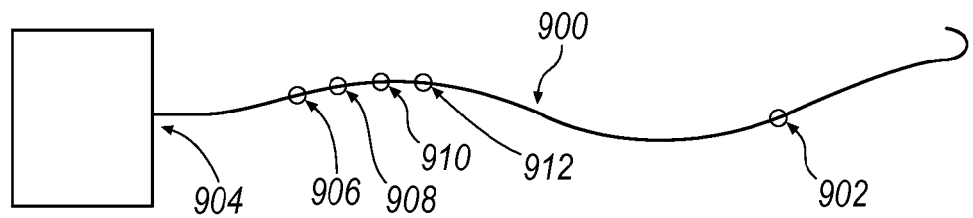
FIG. 9 is a schematic illustration of an exemplary elongate member, e.g., a fiber, having a proximal end and a distal end.
Figure 10:
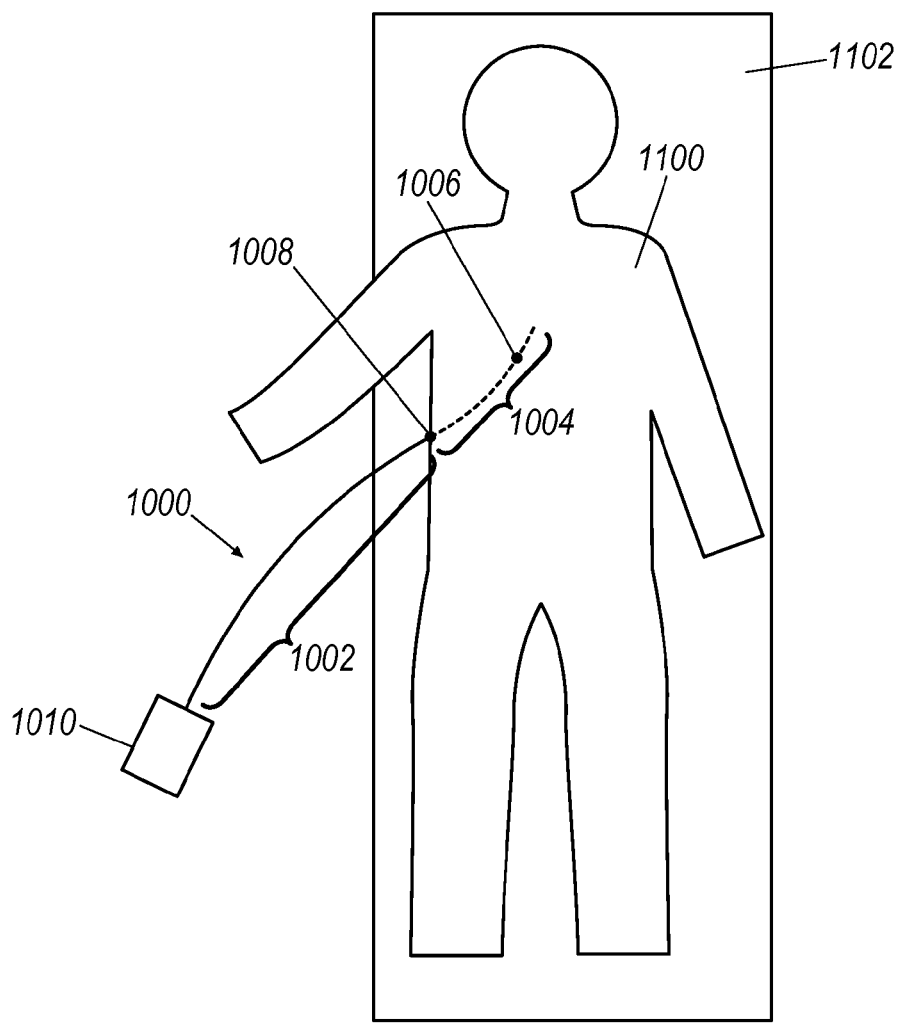
FIG. 10 is a schematic illustration of another exemplary elongate member having a distal end inserted into a patient, with a proximal end remaining outside the patient.
Figure 11:
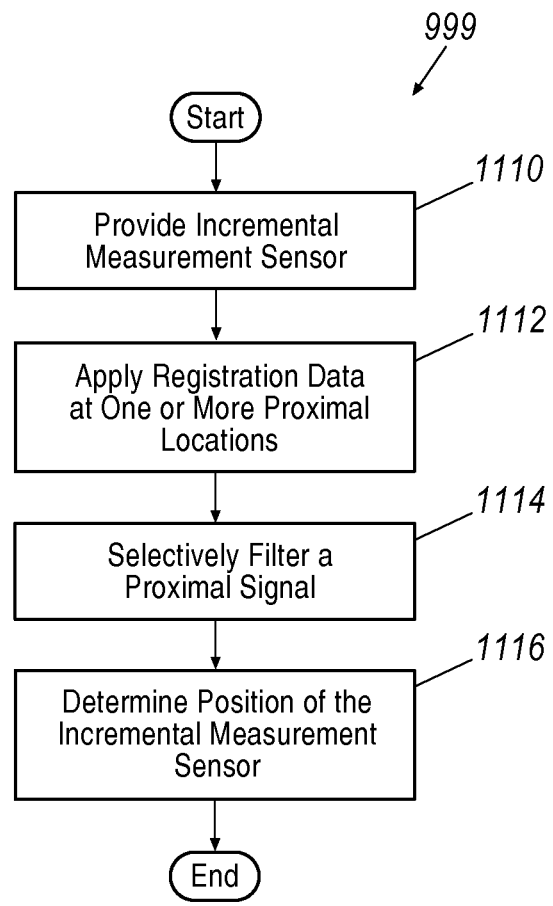
FIG. 11 is a process flow diagram for an exemplary process of reducing measurement error associated with the position of an elongate member.

Turning now to FIGS. 9-11, exemplary systems and methods for reducing measurement error, e.g., of an incremental measurement sensor (IMS), is described in further detail. Registration, as described above, is generally the mathematical process of computing the orientation and position of all or portions of a shape (sequence of points) in some coordinate frame. Registration can fix the orientation and position of the fiber at one or more points (for six degrees of freedom of constraints at each point) or registration can be carried out with fewer constraints at a single point or multiple points. Inherently, though, registration is the method of positioning and orienting a sensor frame in a reference frame.

For any IMS, one type of registration is to determine the position and orientation of the proximal end ("origin" of the IMS) in the fluoroscopy, or world, coordinate frame and display that to the user in the virtual environment. By determining the transformation of the "origin" of the IMS to the world coordinate system, the points in the IMS can be transformed and displayed in the world coordinate system throughout the procedure. However, the accuracy of this registration procedure can be difficult and inadequate for applications that require sub-mm accuracy at the distal end of the sensor. Inaccuracy will result if the origin of the IMS moves; if the origin does move, it needs to be tracked in the world coordinate frame, which may lead to error. In addition, the error inherent in the sensor could cause errors in the sensor measurement. For instance, in a fiber optic shape sensor, the tighter the bends, the less accurate the sensor is. Tight bends that may occur early in the path of the fiber either due to mechanical structures in the device or pathways in the anatomy, cause additional error in the orientation measurement. This orientation error may be magnified by the lever arm of the fiber causing the tip to be inaccurate by centimeters. This is unsuitable for many applications since sub-millimeter accuracy is desired.

Additional Registration Points

In one exemplary approach illustrated in FIG. 9, multiple positions of registration along the length of an elongate member 900 may be provided to reduce the error in a sensor 902. In one example, the sensor 902 is an IMS fiber sensor configured to output a position of the elongate member at the sensor 902. The elongate member, e.g., a catheter, may be generally fixed at a proximal end 904 such that the position of the proximal end 904 may generally be known. A position of the elongate member 900 is known at one additional point 906, which is proximal to the distal portion of the sensor 902. While only one additional point 906 is illustrated, any number of additional points proximal to the sensor 902 may be used, as described further below. Using the additional piece(s) of information at the point(s) proximal to the sensor 902 may be used to register the IMS at a position distal of the "origin," i.e., at the sensor 902, helping to reduce orientation error propagated from the proximal end to a position error in the distal end. The nature of the fiber and catheter is that the proximal end is the only place that the fiber is attached to the system, but there are a number of ways of acquiring registration along the length of the fiber.

Registration of a shape or series of points of the IMS sensor 902 can be used to improve registration. This can be performed by acquiring 3D shapes or obtaining spatial information from 2D images, i.e., of the elongate member 900. For example, a plurality of points 906, 908, 910, and 912 may be employed to determine a shape of the elongate member 900 at each of the points 906, 908, 910, and 912, such that a shape or position of the elongate member 900 is known. There are many sources of a three-dimensional anatomic model in robotic catheter procedures that may be used in this manner. For instance, models could be generated from a rotational angiography, computed tomography scan, or other standard imaging technique. Also, any known shape that the catheter passes through could also contribute to registration just as in a 3-D model, such as an engineered semitortuous introducer, a curve in the take-off of the sheath splayer, an anti-buckling device feature, etc. In all these cases, the catheter and IMS will be passing through a known shape that can be used to register the position and orientation of a distal portion of the catheter.

Once the catheter is known to pass through a given three-dimensional shape defined by the points 906, 908, 910, and 912, providing the registration is an optimization problem to find the most likely position and orientation of the sensed shape in relation to the model of the elongate member 900. This solution could be completed using many standard computer graphics matching techniques or posed as a numeric optimization problem.

Another example of other 3D information may be to add other localization sensors such as an electromagnetic sensor to various critical points along the catheter. More specifically, at least one of the proximal points 906, 908, 910, and/or 912 may have an electromagnetic sensor. The generally absolute measurements of position at these locations can reduce any error propagated from the fiber at a portion distal of the position of any electromagnetic sensors at points 906, 908, 910, and/or 912.

Another exemplary method of obtaining additional shape information is to use computer vision techniques on the fluoroscopy images to track the catheter and then feed that information into the system to improve registration. Because two-dimensional imaging will provide less information than a 3D model it may not provide as much information to reduce error, but it would likely remove error at least in the plane of the image. This registration might also not be needed constantly during a procedure, but may be used when imaging, e.g., fluoroscopy, is active and the operator wants more accuracy of the tracked catheter. Accordingly, a position of a proximal portion of the elongate member 900, e.g., along points 906, 908, 910, and/or 912 may be visualized in 2D and used to increase accuracy of measurements at the sensor 902.

In a way, the above exemplary approaches to optimizing position measurements of the sensor 902 provide an alternate registration location to a proximal portion of the elongate member, e.g., at the base of the fiber at the splayer attached to the RCM. However, in these examples registering a shape to a 3D model does not necessarily completely replace the registration at the splayer (not shown in FIG. 9). Using an optimization technique that finds the most likely position and orientation of the sensor given both the anatomical registration and the distal splayer registration is probably the best way to reduce overall error and achieve a strong overall pose of the catheter in relation to the anatomy. This algorithm can also take advantage of any proximal motion of the catheter, such as shaft insertion, etc. However, this algorithm can be time consuming and computationally intensive, especially when a good starting point is not given. The registration of the origin of the IMS could be used as such a starting point.

Another exemplary approach in the case where global registration of position is not needed would be to allow the user to designate a specific position on the catheter that is constrained laterally, e.g., by the anatomy of a patient. For example, as shown in FIG. 10 an elongate member 1000 is partially inserted into a patient 1100, who remains generally fixed in position on a table 1102. In this manner, a distal portion 1004 of the elongate member 1000, which includes an IMS 1006 for measuring position of the elongate member 1000, is received within the patient 1100, while a proximal portion 1002 remains outside the body of the patient 1100. The insertion site 1008 of the elongate member 1000 into the patient 1100 is known and is substantially fixed, such that a position of the elongate member 1000 is known at the insertion site 1008 in at least two dimensions. The insertion site 1008 position, at least in two degrees of freedom, could be registered in addition to the splayer 1010, while the insertion of the elongate member 1000 is updated accordingly. With this technique, the orientation of the elongate member 1000 and/or a measurement fiber at this designated 'base' (i.e., the insertion site 1008) of the shorter effective fiber would depend on the actual orientation of the fiber (including twist) and the insertion would depend on the commanded fiber insertion. However, the shape distal to the insertion site 1008 could be updated rapidly and without any error from the shape of the proximal portion 1002, which is proximal to the designated base position, i.e., the insertion site 1008. Accordingly, error in position measurements of the elongate member 1000 anywhere along the distal portion 1004 is greatly reduced by effectively reducing the measurement length of the IMS 1006.

The above exemplary approach may be particularly advantageous for relative position display (essentially a coordinate frame not correctly registered to the fluoroscopy/anatomical coordinate frames) but may ultimately make it difficult to determine a global position of the tip of the catheter. However, in many applications that do not superimpose the catheter directly over a model of anatomy (or imply perfect registration) it would be perfectly appropriate.

Selective Filtering

Other exemplary approaches are generally based around the idea that filtering is a method of sacrificing responsiveness in the time domain to reduce the shape and position error. For example, an operator of an elongate member may generally be focusing on the distal end of the catheter during a procedure, and the proximal end will generally be stable and not moving quickly. As a result, selective filtering on proximal shape can be applied to reduce orientation error in the proximal region while the distal region does not filter the signal. More specifically, in the example shown in FIG. 9, position data associated with the distal region of the elongate member 900 between the points 912 and 902 is not filtered, while the position data of a proximal region between points 906 and 912 is filtered. The selective filtering of the proximal region reduces the influence of proximal error by filtering it out (for instance, averaging over multiple time steps) while, the distal portion will be updated as fast as possible using the orientation and position of the proximal section as a stable base.

In one exemplary illustration, one could average the positions and orientation over time in the global frame, or you could average incremental changes in orientation over time and then integrate the averaged orientation changes to yield the final shape. Integrating the incremental changes could be a more accurate average particularly in the case of a fiber-based measurement system, e.g., FOSSL, because the actual measurement is being determined from an indication of strain, which is proportional to bend angle and orientation. Thus, white noise may be present on the level of the strain/incremental orientation as opposed to the final incremented position and orientation.

Because the attention of the operator will likely be focused on the distal tip or portion, the result of proximal filtering will be a responsive system that exhibits less error. The exact location where filtering starts or stops may vary based on the application and it is even possible to apply a variable level of filtering along the fiber with the maximum filtering at the proximal end, e.g., between points 906 and 912, and the minimum at the distal end, e.g., distal of the point 902. In one case when absolute registration is not needed, it is simple to ignore the proximal portion(s) of the fiber and treat the distal portion of the fiber as a non-grounded shape sensor that can be oriented arbitrarily.

In examples where the proximal end is filtered heavily in relation to the distal end, it may be useful to detect when the proximal shape changes significantly in a short period of time, such as a prolapsed catheter at the iliac bifurcation (a rapid motion of the shaft of the catheter bulging up into the aorta). This can be accomplished by noting when the new catheter shape is significantly different than the filtered shape. In this case, the filtering on the proximal end can be reduced so that the operator sees the most up to date information and can react accordingly. After the proximal shape remains more constant for a period of time, the filtering can increase, again reducing error at the tip. To prevent sudden jumps in the rendered data, temporarily-variable filtering algorithms can be implemented in such a way as to provide continuity of the filter output, which may increase the appearance of smoothness and reduce noise of the measurement.

An anatomical model need not be used to separate distal and proximal updates of an IMS localization technology. One exemplary approach would be to apply relatively heavy filtering on the proximal end of the fiber, e.g., between points 906 and 912, and light filtering on the distal end, e.g., distal of point 902, as described above. Specific aspects of this sensor when used in a robotic system could modified, such as updating insertion immediately without filtering since axially the catheter is relatively stiff and low in error (assuming the catheter does not buckle). This is potentially problematic because by filtering different dimensions at different rates, trajectories can become skewed, producing measurement points that do not lie along the true trajectory of the device. Additionally, filtering could be accelerated when the proximal measurement changes significantly in relation to the filtered version to give more responsive feedback during a prolapsed situation.

It should be noted that instinctiveness computations are often computed from orientations propagated from the registered base of the fiber. Instinctiveness refers generally to matching and orientation or a location of a device such as a catheter with a visualization device that is used to control the catheter, such as an image of the catheter. Since instinctiveness includes absolute orientation measurements, they may be computed separate from any intermediate registration or clipping techniques. On the flip side, because distance does not magnify orientation errors, there is little or no extra error from the distance from the base to the tip of the fiber in instinctiveness measurements. Furthermore, instinctiveness measurements generally do not require a fast update rate so it is possible to filter heavily to reduce orientation error and noise.

Turning now to FIG. 11, an exemplary process 999 for determining a position of a distal portion of an elongate member is illustrated. Process 999 may begin at block 1110, where an incremental measurement sensor may be provided. For example, as described above an elongated member 900 may have an IMS 902 positioned along a distal portion of the elongate member 900. In some exemplary approaches, the elongate member 900 includes a fiber, which may be employed to determine position and/or orientation data of the elongate member 900. Process 999 may then proceed to block 1112.

At block 1112, registration data may be applied at one or more proximal locations along the elongated member. For example, as described above a position of the elongate member 900 at any one or more of points 906, 908, 910, and/or 912 may be registered. For example, a proximal position of one or more proximal locations may be used to increase accuracy of measured data from the IMS 902.

In some examples, one of the proximal locations used to apply registration data along the elongated member 900 includes a proximal attachment of the elongated member 900, e.g., at a proximal end 904. The proximal attachment at the proximal end 904 may general fix a portion of the elongated member at the first one of the locations. In other examples, a position of the proximal location(s) may be determined using an electromagnetic sensor, or by using a two-dimensional image of the one or more proximal locations, e.g., as obtained by fluoroscopy during a procedure. In still another example, applying the registration data at the one or more proximal locations may include constraining a lateral position of the one or more proximal locations. Merely as one example, as described above an insertion site 1008 associated with a patient 1100 may generally constrain an elongate member 1000 laterally at the insertion site 1008. Accordingly, the generally fixed insertion site 1008 indicates a position of the elongate member 1000 in at least two dimensions at the insertion site 1008.

Proceeding to block 1114, a proximal signal of the elongated member may be selectively filtered, e.g., in relation to a distal signal of the elongated member. Filtering of the proximal signal may occur at a different rate than the filtering of the distal signal. In one example, heavier or more intrusive filtering of the proximal signal may be employed, especially during a procedure where the proximal portion(s) of the elongate member do not change rapidly. In some cases, filtering may include averaging an incremental orientation position change in the proximal signal. Moreover, variable filtering methodologies may be used. For example, as described above a heavier filtering methodology may be employed only during such times that a position of the proximal portion of the elongate member is not rapidly changing position. Upon detection of a rapid or unexpected change, the filtering of the proximal portion may cease or be reduced. Filtering at the initially heavier setting may resume after a predetermined period of time expires, in which the proximal portion of the elongate member maintains a same position or does not rapidly change position during such time. Process 999 may then proceed to block 1116.

At block 1116, a position of the incremental measurement sensor may be determined. For example, as described above a position of an IMS 902 may be determined based at least upon the registration data from the one or more proximal locations. In this manner, measurement error may be reduced since less incremental error occurs over the length of the elongate member. Alternatively, or in addition, a position of the incremental measurement sensor may be determined based at least upon a filtered proximal signal. In such cases, selectively filtering may reduce a fluctuation of the determined position of incremental measurement sensor by generally smoothing out position signals relating to the proximal portion(s) of the elongate member.

CONCLUSION

The methods described above are the examples of registration using known data about the location of the catheter in relation to the anatomy. The first example does not include extra localization information while the second example assumes some knowledge of the shape of the anatomy or other features along the path of the catheter. Between these examples, there are a number of other ways to get partial registration at one or more points along the fiber to reduce orientation error propagated down the fiber.

The exemplary systems and components described herein, including the various exemplary user interface devices, may include a computer or a computer readable storage medium implementing the operation of drive and implementing the various methods and processes described herein. In general, computing systems and/or devices, such as user input devices included in the workstation 31 or any components thereof, merely as examples, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., and the Android operating system developed by the Open Handset Alliance.

Computing devices generally include computer-executable instructions, where the instructions may be executable by one or more computing devices such as those listed above.

Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain examples, and should in no way be construed so as to limit the claims.

Accordingly, it is to be understood that the above description is intended to be illustrative and not restrictive. Many examples and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future examples. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various examples for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method of determining a position of an elongated member, comprising:
   providing an incremental measurement sensor at a distal position on an elongated member;
   applying registration data at one or more proximal locations along the elongated member; and
   determining a position of the incremental measurement sensor based at least upon the registration data from the one or more proximal locations.

2. The method of claim 1, further comprising establishing a first one of the one or more locations along the elongated member as including a proximal attachment of the elongated member, the proximal attachment generally fixing a portion of the elongated member at the first one of the locations.

3. The method of claim 1, wherein applying the registration data at the one or more proximal locations includes determining a proximal position of the one or more proximal locations.

4. The method of claim 3, further comprising determining the proximal position of the one or more proximal locations with an electromagnetic sensor.

5. The method of claim 3, further comprising determining the proximal position of the one or more proximal locations using a fluoroscopy image of the one or more proximal locations.

6. The method of claim 1, wherein applying the registration data at the one or more proximal locations includes constraining a lateral position of the one or more proximal locations.

7. The method of claim 1, further comprising selectively filtering a proximal signal of the elongated member.

8. The method of claim 7, further comprising determining the position of the incremental measurement sensor based at least upon the filtered proximal signal, thereby reducing a fluctuation of the determined position of incremental measurement sensor.

9. The method of claim 7, further comprising filtering a distal signal of the elongated member.

10. The method of claim 9, further comprising establishing the filtering of the proximal signal at a different rate than the filtering of the distal signal.

11. The method of claim 7, further comprising establishing the selective filtering as including averaging an incremental orientation change in the proximal signal.

12. The method of claim 1, further comprising establishing the elongated member as a fiber.

13. A method of determining a position of an elongated member, comprising:
   providing an incremental measurement sensor at a distal position on an elongated member;
   selectively filtering a proximal signal of the elongated member; and
   determining a position of the incremental measurement sensor based at least upon the filtered proximal signal, thereby reducing a fluctuation of the determined position of incremental measurement sensor.

14. The method of claim 13, further comprising determining the position of the incremental measurement sensor based at least upon the filtered proximal signal, thereby reducing a fluctuation of the determined position of incremental measurement sensor.

15. The method of claim 13, further comprising filtering a distal signal of the elongated member.

16. The method of claim 15, further comprising establishing the filtering of the proximal signal at a different rate than the filtering of the distal signal.

17. The method of claim 13, further comprising applying registration data at one or more proximal locations along the elongated member, and determining the position of the incremental measurement sensor based at least upon the registration data.

18. The method of claim 13, further comprising establishing the elongated member as a fiber.

19. A measurement system, comprising:
   an incremental measurement sensor positioned at a distal position on an elongated member; and
   a processor configured to apply registration data at one or more proximal locations along the elongated member, wherein the processor is configured to determine a position of the incremental measurement sensor based at least upon the registration data from the one or more proximal locations.

20. The system of claim 19, wherein the processor is configured to selectively filter a proximal signal of the elongated member, the processor configured to determine a position of the incremental measurement sensor based at least upon the filtered proximal signal, thereby reducing a fluctuation of the determined position of incremental measurement sensor.

* * * * *